Figure 1:
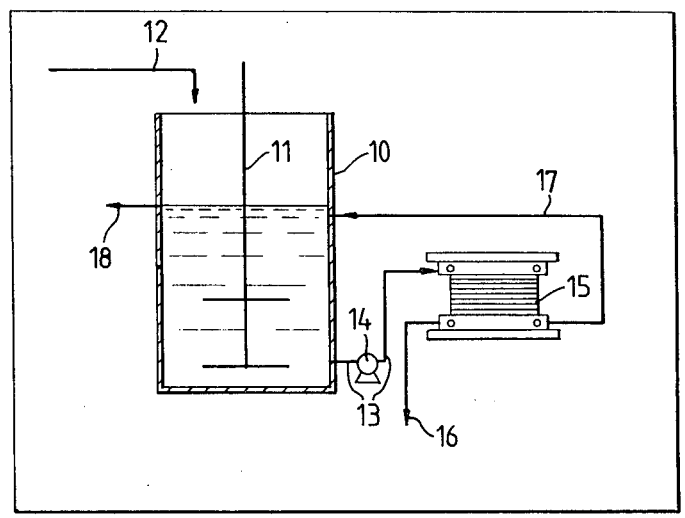

United States Patent [19]

Rogers et al.

[11] 4,443,544

[45] Apr. 17, 1984

[54] ETHANOL PRODUCTION IN A CONTINUOUS PROCESS WITH CELL RECYCLE

[75] Inventors: Peter L. Rogers, Northwood; David E. Tribe, Maroubra, both of Australia

[73] Assignee: Unisearch Limited, Kensington, Australia

[21] Appl. No.: 240,140

[22] Filed: Mar. 3, 1981

[30] Foreign Application Priority Data

Mar. 5, 1980 [AU] Australia .............................. PE2655
May 15, 1980 [AU] Australia .............................. PE3561

[51] Int. Cl.$^3$ ............................................... C12P 7/14
[52] U.S. Cl. .................................... 435/162; 435/801; 435/813; 435/822
[58] Field of Search ................ 435/161, 162, 163–165, 435/801, 813, 822

[56] References Cited

FOREIGN PATENT DOCUMENTS 2013716 8/1979 United Kingdom .

OTHER PUBLICATIONS

Rogers et al., "Kinetics of Alcohol Production by *Zymomonas mobilis* at High Sugar Concentrations", Chemical Abstracts, vol. 91 (1979), Abstract No. 3905p.
Lee et al., "Ethanol Production by *Zymomonas mobilis* in Continuous Culture at High Glucose Concentrations", Chemical Abstracts, vol. 92 (1980), Abstract No. 4686a.

*Primary Examiner*—R. B. Penland
*Attorney, Agent, or Firm*—Murray & Whisenhunt

[57] ABSTRACT

An improved method for the production of ethanol from a fermentable carbohydrates such as glucose, fructose or sucrose using the bacterium *Zymomonas mobilis* which method involves continuously culturing the bacterium in a culture medium containing the fermentable carbohydrate, continuously drawing off a portion of the culture medium and replacing that portion with fresh culture medium, separating from the removed portion of the culture medium cells of *Zymomonas mobilis* contained therein and returning those cells to the culture medium and recovering the ethanol contained in the portion of the culture medium from which the cells have been removed.

It has been found that this method results in greatly improved ethanol production without the disadvantages which have been found when yeasts are continuously cultured.

7 Claims, 1 Drawing Figure

ETHANOL PRODUCTION IN A CONTINUOUS PROCESS WITH CELL RECYCLE

The present invention relates to a method for the production of ethanol (alcohol) using the bacterium *Zymomonas mobilis*.

It is known to use the bacterium *Zymomonas mobilis* for the production of ethanol, and in fact this bacterium is used for the production of palm wine and other alcoholic beverages in tropical countries. It is also known that theoretically the production of ethanol using this bacterium has certain advantages as compared with yeasts which are conventionally used to produce alcohol by the fermentation of sugars, starches and other carbohydrate substrates. These advantages include the fact that *Zymomonas mobilis* produces less biomass than do yeasts due to the lower energy available for growth inherent in the Entner-Doudoroff pathway used by the bacterium which yields only one mole of ATP per mole of glucose metabolised as compared with the glycolytic pathway used by yeasts which yields two moles of ATP per mole of glucose. A further potential advantage is that *Zymomonas mobilis* grows anaerobically.

The present inventors have found that greatly increased ethanol productivity can be achieved by continuously culturing *Zymomonas mobilis* with cell recycle. It has been discovered, and this could not have been predicted a priori, that continuous culture with cell recycle of *Zymomonas mobilis* does not suffer from the difficulties encountered with continuous culture with cell recycle of conventional yeasts. These difficulties include the need to provide sterile oxygen to maintain yeast cell viability at high yeast concentrations, and the likelihood of contamination by unwanted bacteria during the extended period of continuous operation.

With *Zymomonas mobilis* fermentation using continuous culture with cell recycle as well as achieving higher ethanol productivities as compared with other techniques for *Zymomonas mobilis* fermentation and as compared with yeast fermentation, it has been found that there is no requirement for oxygen to maintain viability at high cell concentrations. Furthermore due to the faster rates of sugar uptake and enhanced ethanol tolerance when compared to yeasts it has been found that no contamination occurs during extended periods of continuous operation.

The present invention consists in a process for the production of ethanol from a medium containing a fermentable carbohydrate continuously culturing *Zymomonas mobilis* in the culture medium, continuously or periodically drawing off a portion of the culture medium and replacing that portion with fresh culture medium, separating from the withdrawn portion of the culture medium cells of *Zymomonas mobilis* contained therein, returning the cells to the culture medium, and recovering the ethanol contained in the portion of the culture medium from which the cells have been removed.

The process according to the present invention is preferably carried out at a temperature of from 20° C. to 50° C., most preferably at 25° to 40° C., and at a pH between 3.7 and 8, most preferably 4.5 to 6.5. The medium preferably contains from 100 to 400 g/l of a fermentable carbohydrate, most preferably from 150 to 300 g/l.

The preferred carbohydrates for use as fermentable substrates in the culture medium include, in addition to glucose, simple sugars such as fructose lactose and sucrose, starch and starch hydrolysates, and cellulosic raw materials. It will be recognised that any one strain of *Zymomonas mobilis* will probably not ferment all of these substrates and therefore for any particular strain a suitale, fermentable, substrate should be selected.

It is preferred that the strain of *Zymomonas mobilis* used in this process is a strain having a high specific ethanol productivity, a high specific rate of glucose uptake and a high alcohol tolerance. A particularly suitable organism is CP4 from the type culture collection of:

Dr. J. De Ley
Laboratory of Microbiology,
Ledeganckstraat 35,
B - 900 GENT
Belgium Mutants of this strain have also been found to be particularly useful in carrying out the present process and may have a broader range of fermentable substrates than CP4 itself. The mutant strains may be produced by mutations of an existing strain as by the use of U.V. radiation or nitrosoguanidine. Desirable properties may also be introduced into the *Zymomonas mobilis* strains by plasmid transfer from other bacteria using, for example, membrane filter mating techniques.

The separation of the cells from the removed portion of the culture medium may be achieved in any suitable manner. The cells may be removed by the use of a cross-flow microfiltration membrane system, preferably using a membrane having a pore size of the order of 0.6 microns. Alternatively the cells may be separated in a centrifuge or in a series of hydroclones. If flocculent *Zymomonas mobilis* cells are used these may be removed from the culture medium by allowing them to settle in a settling vessel or a series of hydroclones.

The strains of *Zymomonas mobilis* referred to in this specification have been deposited in the American Type Culture Collection, 12301 Park Lawn Drive Rockville, Md. 20852, U.S.A. and have been assigned the following deposit numbers and dates:

| Specification Reference | ATCC Deposit No. | Deposit Date |
| --- | --- | --- |
| CP4 | 31821 | February 26, 1981 |
| ZM481 | 31823 | February 26, 1981 |
| ZM401 | 31822 | February 26, 1981 |

EXAMPLES

In the following examples the bacterium *Zymomonas mobilis* was cultured in a fermentation medium comprising the following nutrient concentrations:

100–300 g/l glucose
5 g/l yeast extract
1 g/l $(NH_4)_2 SO_4$
1 g/l $KH_2 PO_4$
0.5 g/l $MgSO_4\, 7H_2O$ The cultures of the various strain of *Zymomonas mobilis* were maintained by transferring to fresh agar slants containing 20 g glucose, 10 g yeast extract and 20 g agar at pH 5.0 each week and storing at room temperature.

The continuous fermentation system was controlled at a temperature of 30° C. and pH 5.0 in a 1 liter fermentation vessel. The pH was controlled by the addition of 2 N NaOH.

In these experiments cell recycle was carried out using a cross-flow microfiltration membrane system including a "Millipore" membrane BD having a nominal pore size of 0.6 microns. This membrane retained all cells and the permeate passing through the membrane was free from cells and contained the same ethanol concentration as the contents of the fermenter.

FIG. 1 shows the arrangement of the fermenter and cell recycle system. In this FIGURE 10 is a fermentation vessel fitted with a stirrer 11. The culture medium is introduced into the fermenter 10 through line 12 and is drawn off through line 13 to a pump 14 and thence to a tangential flow microfilter 15. The permeate through the filter 15 is discharged through line 16 to storage prior to recovery of the ethanol therefrom while the retained cell concentrate is returned through line 17 to the fermenter 10. An overflow line 18 is provided.

Table I shows the greatly improved maximum ethanol productivity of three strains of Zymomonas mobilis continuously cultured with cell recycle as compared with two strains of the yeast Saccharomyces Cerevisiae.

TABLE I

| Organism | Glucose $Conc^n$ (g/l) | Ethanol $Conc^n$ (g/l) | Maximum Productivity (g/l/h) |
| --- | --- | --- | --- |
| S. Cerevisiae (ATCC 4126) | 100 | 43 | 29 |
| S. Cerevisiae (NRRL Y-132) | 150 | 61 | 32 |
| Z. Mobilis (ATCC 10988) | 100 | 45 | 120 |
| Z. Mobilis (CP4) | 140 | 65 | 200 |
| Z. Mobilis (ZM 481) | 180 | 85 | 85 |

From the above table it is clear that the continuous culture of Zymomonas mobilis with cell recycle can give productivities which are 200 to 300% higher than for yeasts fermentations carried out under similar conditions. This means that the size of the fermentation vessels to produce ethanol may be reduced by an equivalent amount.

The organism Zymomonas mobilis ZM 481 was developed from strain CP4 as follows:

Strain CP4 was grown statically at 30° C. until it was in the exponential growth phase. Nitrosoguanidine was then added to a final concentration of 50 ug/ml and the culture was incubated for 30 minutes at 30° C. The cells were then washed twice in saline phosphate buffer and regrown overnight at 30° C. The culture was then plated on plates containing 10%(v/v) ethanol. After several days incubation at 30° C., mutant colonies appeared at a frequency of approximately $10^{-7}$, and these were purified on similar medium and then tested for growth and ethanol production rates with 100, 200 and 250 g/l glucose, at 30° C. in tubes. The culture which produced the highest level of ethanol in the shortest time was numbered ZM48.

A second similar mutagenesis was done with strain ZM48 but the cells were plated with 15% (v/v) ethanol. The mutant which produced the highest level of ethanol in the shortest time was numbered ZM481, and was kept as an ethanol tolerant strain in the type culture collection in the School of Biotechnology, University of New South Wales, Sydney, New South Wales, Australia.

The use of flocculent strains of Zymomonas mobilis in the present invention is advantageous. Table II records the use of a flocculent strain of Zymomonas mobilis using a settling column as compared with a flocculent strain of Saccharomyces cerevisiae.

In the following Table the results with a flocculent strain of Zymomonas mobilis are compared with the results for a flocculent strain of Saccharomyces cererisiae.

TABLE II

| Organism | Glucose $Conc^n$ (g/l) | Ethanol $Conc^n$ (g/l) | Maximum Productivity (g/l/h) |
| --- | --- | --- | --- |
| S. Cerevisiae (ATCC 4126) | 100 | 43 | 29 |
| Z. Mobilis (ZM 401) | 100 | 45 | 51 |

The flocculent mutant ZM 401 was isolated as follows. A culture of strain CP4 was grown in rich medium, RM, (20 g/l glucose, 10 g/l yeast extract, 2 g/l $KH_2PO_4$) statically at 30° C. until it was in the exponential phase of growth. Then nitrosoguanidine (NTG) was added to a final concentration of 50 ug/ml and the culture was further incubated for 1 hour. The cells were then washed twice in saline phosphate buffer, and incubated statically overnight in RM at 30° C. After this time, a few small granular flocs were visible at the bottom of the flask. The supernatant medium, with the majority of cells was carefully removed, and fresh medium was added. After repeatedly subculturing every 24 hours in this manner for 7 days, an apparently pure culture of granular flocs was obtained. This culture was streaked on RM plates twice to further purify it by single colony isolation. A single colony was then retested in liquid medium, and was still flocculent. This was chosen as the flocculent strain, and was renumbered ZM 401.

From the Table it is clear that ZM 401 has considerable advantages, in terms of enhanced productivities, over strains of flocculent yeast.

Table III shows the greatly increased ethanol productivity using a continuous culture with cell recycle of Zymomonas mobilis (ATCC 10988) as compared with the batch culture and continuous culture without cell recycle of the same organism all in medium containing 100 g/l of glucose.

TABLE III

| Cultivation Type | Ethanol Productivity (g/l/h) |
| --- | --- |
| Batch | 5 |
| Continuous | 11 |
| Continuous with cell recycle | 120 |

It can be seen that there is a ten fold increase in the ethanol productivity as between continuous culture of the organism and continuous culture with cell recycle.

We claim:

1. A process for the production of ethanol from a culture medium containing a fermentable carbohydrate, said process consisting essentially of continuously anaerobically culturing Zymomonas mobilis in the culture medium, continuously or periodically drawing off a portion of the culture medium to give a withdrawn portion and replacing that portion with fresh culture medium, separating from the withdrawn portion of the culture medium cells of *Zymomonas mobilis* contained therein, returning said cells to the culture medium, and recovering the ethanol contained in the portion of the culture medium from which said cells have been removed.

2. A process as claimed in claim 1 in which the fermentable carbohydrate is selected from the group consisting of glucose, fructose and sucrose.

3. A process as claimed in claim 1 in which the cells are recovered from the withdrawn portion of the culture medium by filtration.

4. A process as claimed in claim 1 in which the cells are flocculent and are recovered from the withdrawn portion of the culture medium in a settling vessel.

5. A process as claimed in claim 1 in which the culture medium is maintained at a temperature between 20° C. and 50° C.

6. A process as claimed in claim 1 in which the culture medium is maintained at a pH between 3.7 and 8.

7. A process for the production of ethanol from a culture medium containing a fermentable carbohydrate, said process comprising continuously culturing a strain of *Zymomonas mobilis* selected from the group consisting of CP4, ZM481 and ZM401 in the culture medium, continuously or periodically drawing off a portion of the culture medium to give a withdrawn portion and replacing that portion with fresh culture medium, separating from the withdrawn portion of the culture medium said cells of *Zymomonas mobilis* contained therein, returning said cells to the culture medium, and recovering the ethanol contained in the portion of the culture medium from which said cells have been removed.

* * * * *